(12) United States Patent
Dubois

(10) Patent No.: US 8,394,973 B2
(45) Date of Patent: Mar. 12, 2013

(54) MANUFACTURE OF MALEIC ANHYDRIDE FROM RENEWABLE MATERIALS, MALEIC ANHYDRIDE OBTAINED, AND USES THEREOF

(75) Inventor: Jean-Luc Dubois, Millery (FR)

(73) Assignee: Arkema France, Colombes Cedex (FR)

( * ) Notice: Subject to any disclaimer, the term of this patent is extended or adjusted under 35 U.S.C. 154(b) by 242 days.

(21) Appl. No.: 13/003,083

(22) PCT Filed: Jul. 17, 2009

(86) PCT No.: PCT/FR2009/051426
§ 371 (c)(1),
(2), (4) Date: Jan. 7, 2011

(87) PCT Pub. No.: WO2010/007327
PCT Pub. Date: Jan. 21, 2010

(65) Prior Publication Data
US 2012/0015411 A1   Jan. 19, 2012

(30) Foreign Application Priority Data

Jul. 18, 2008   (FR) ...................................... 08 54896

(51) Int. Cl.
*C07D 303/38* (2006.01)
*C07K 1/00* (2006.01)
(52) U.S. Cl. ........................................ 549/260; 530/350
(58) Field of Classification Search .................. 549/260; 530/350
See application file for complete search history.

(56) References Cited

FOREIGN PATENT DOCUMENTS

GB                 790559       *    2/1958

* cited by examiner

*Primary Examiner* — Maryam Monshipouri
(74) *Attorney, Agent, or Firm* — Smith, Gambrell & Russell, LLP

(57) ABSTRACT

The present application relates to a process for manufacturing maleic anhydride that comprising the following steps: a) fermentation of renewable raw materials and optionally purification to produce a mixture comprising at least butanol; b) oxidation of the butanol to maleic anhydride at a temperature generally between 300° C. to 600° C., using a catalyst based on oxides of vanadium and/or molybdenum; c) isolation of the maleic anhydride obtained at the end of step b). It also relates to the maleic anhydride obtained from renewable raw materials, to the copolymers and compositions comprising said maleic anhydride and also uses of use of this maleic anhydride.

5 Claims, No Drawings

MANUFACTURE OF MALEIC ANHYDRIDE FROM RENEWABLE MATERIALS, MALEIC ANHYDRIDE OBTAINED, AND USES THEREOF

This application is a 371 of PCT/FR09/51426, filed Jul. 17, 2009, which claims foreign priority to French Patent Application No. 0854896, filed Jul. 18, 2008.

FIELD OF THE INVENTION

The present invention relates to a process for manufacturing maleic anhydride from renewable raw materials.

BACKGROUND OF THE INVENTION

In particular, the invention relates to a process for manufacturing maleic anhydride from alcohols derived from the fermentation of renewable raw materials; preferably, the renewable raw materials are vegetable matter.

Maleic anhydride is generally obtained by oxidizing aromatic compounds, especially benzene, or by oxidizing alkanes, especially n-butane.

In recent years, essentially because of the growing awareness of the toxicity of benzene and the increase in the cost of producing it, pathways for the synthesis of maleic anhydride starting from other raw materials have been investigated. Benzene is in fact obtained from non-renewable raw materials of fossil origin (oil). However, oil resources are limited; extracting oil requires excavating deeper and deeper under tougher and tougher technological conditions, necessitating sophisticated equipment and the use of processes which consume more and more energy. These constraints have a direct consequence for the cost of manufacturing maleic anhydride.

Another synthesis pathway is currently more widely used, namely the oxidation of butane; however, butane is also obtained from oil and/or from natural gas fractions.

Advantageously and surprisingly, the inventors of the present application have developed a process for the industrial manufacture of maleic anhydride from renewable raw materials.

The process of the invention means that at least a portion of the raw materials of fossil origin can be dispensed with and replaced by renewable raw materials.

The maleic anhydride obtained using the process of the invention is of a quality such that it can be used in all applications where the use of maleic anhydride is known. In particular, the inventors have shown that it is possible to produce a maleic anhydride of higher purity by using the process of the invention, which uses renewable raw materials rather than raw materials of fossil origin.

DETAILED DESCRIPTION OF THE INVENTION

The invention provides a process for manufacturing maleic anhydride, comprising the following steps:
a) fermenting renewable raw materials and optional purification in order to produce a mixture comprising at least butanol;
b) oxidizing butanol to maleic anhydride at a temperature that is generally in the range 300° C. to 600° C. using a catalyst based on oxides of vanadium and/or of molybdenum;
c) isolating the maleic anhydride obtained at the end of step b).

The invention also concerns maleic anhydride that is capable of being produced by the process of the invention, or more generally maleic anhydride obtained from renewable raw materials.

The invention also concerns the uses of maleic anhydride.

Other aims, aspects and characteristics of the invention will become apparent from the following description.

Step a) of the process for manufacturing maleic anhydride in accordance with the invention comprises fermenting renewable raw materials to produce a mixture comprising at least butanol.

A renewable raw material is a natural resource, for example animal or vegetable, wherein the stock can be reconstituted over a short period on a human scale. In particular, this stock has to be capable of renewing itself as quickly as it is consumed. As an example, vegetable matter has the advantage of being capable of being cultivated without its consumption resulting in a conspicuous diminution in natural resources.

In contrast to materials derived from fossil matter, renewable raw materials contain $^{14}C$. All samples of carbon extracted from living organisms (animal or vegetable) are in fact a mixture of 3 isotopes: 120 (representing approximately 98.892%), $^{13}C$ (approximately 1.108%) and $^{14}C$ (traces: $1.2 \times 10^{-10}$%). The $^{14}C/^{12}C$ ratio for living tissue is identical to that of the atmosphere. In the environment, $^{14}C$ preponderantly exists in two forms: in the form of carbon dioxide ($CO_2$) and in the organic form, i.e. carbon integrated into organic molecules.

In a living organism, the $^{14}C/^{12}C$ ratio is kept constant by the metabolism since carbon is continuously exchanged with the external environment. The proportion of $^{14}C$ is constant in the atmosphere, and the same is true in the organism while it is alive, since it absorbs this $^{14}C$ to the same degree as ambient $^{12}C$. The mean $^{14}C/^{12}C$ ratio is equal to $1.2 \times 10^{-12}$.

$^{12}C$ is stable, i.e. the number of atoms of $^{12}C$ in a given sample is constant over time. $^{14}C$ is radioactive; the number of atoms of $^{14}C$ in a sample decreases with time (t); its half-life is equal to 5730 years.

The quantity of $^{14}C$ is substantially constant from extraction of the renewable raw materials until the maleic anhydride of the invention is manufactured and even until said maleic anhydride of the invention has finished being used.

As a consequence, the presence of $^{14}C$ in a material, irrespective of its quantity, gives an indication of the origin of the molecules constituting it, namely that it derives from renewable raw materials and not from fossil materials.

The quantity of $^{14}C$ in a material can be determined by one of the methods described in standard ASTM D6866-06 (Standard Test Methods for Determining the Biobased Content of Natural Range Materials Using Radiocarbon and Isotope Ratio Mass Spectrometry Analysis).

That standard includes three methods for measuring organic carbon derived from renewable raw materials; it is also termed biobased carbon. The proportions indicated for the maleic anhydride of the invention are preferably measured using the mass spectrometry method or the liquid scintillation method described in that standard, more preferably by mass spectrometry.

Those measurement methods evaluate the $^{14}C/^{12}C$ isotope ratio in the sample and compare them with a $^{14}C/^{12}C$ isotope ratio in a material of biological origin providing the 100% standard in order to measure the percentage of organic carbon of the sample.

Preferably, the maleic anhydride obtained from matter of renewable origin of the invention comprises a quantity of carbon derived from renewable raw materials of more than 20%, preferably more than 50% by weight with respect to the total mass of carbon of the maleic anhydride.

In other words, the maleic anhydride may comprise at least $0.24 \times 10^{-10}\%$ by weight of $^{14}C$, preferably at least $0.6 \times 10^{-10}\%$ by weight of $^{14}C$.

Advantageously, the quantity of carbon derived from renewable raw materials is more than 60%, preferably more than 70%, more preferably 80%.

Such a content may, for example, be obtained by mixing butanol of oil origin and butanol derived from renewable raw materials.

The butanol of oil origin may, for example, be obtained by hydroformylating propylene to n-butyraldehyde, followed by hydrogenation to n-butanol.

Vegetable matter, matter of animal origin or matter derived from recovered materials of vegetable or animal origin (recycled materials) may be used as the renewable raw materials.

The vegetable matter in particular includes sugars, starches as well as any vegetable matter containing sugars, cellulose, hemicellulose and/or starches.

The vegetable matter containing sugars is essentially sugar cane and sugar beet; the following may also be cited: maple, date palm, sugar palm, sorghum, American aloe; examples of matter containing cellulose and/or hemicellulose are wood, straw, corn cobs, grain or fruit meal; vegetable matter containing starches are essentially cereals and legumes such as corn, durum wheat, barley, sorghum, rye, wheat, rice, potato, cassava, sweet potato or algae.

Examples of matter derived from recovered materials that may in particular be cited are vegetable or organic waste comprising sugars and/or starches and also any fermentable waste.

Advantageously, low quality raw materials can be used such as potatoes that have been frozen, cereals contaminated by mycotoxins or surplus sugar beet, or whey from cheesemakers.

Preferably, the renewable raw materials are vegetable matter.

Examples of renewable raw materials that may also be employed are cellulose and/or hemicellulose which, in the presence of suitable microorganisms, can be transformed into matter comprising sugar, in particular containing 5 and 6 carbon atoms. Such renewable matter includes straw, wood and paper, which may advantageously derive from recovered materials.

The renewable matter is fermented in the presence of one or more suitable microorganisms; said microorganism may optionally have been modified naturally, by a chemical or physical constraint, or genetically, whereupon it is termed a mutant. Conventionally, the microorganism used is a *Clostridium*, advantageously *Clostridium acetobutylicum* or one of its mutants.

The lists presented hereinabove are not limiting.

The fermentation step may also be preceded by a step for hydrolysis of the raw materials using a cellulase type enzyme or a complex of several cellulase type enzymes.

Fermentation generally results in the production of a mixture of products; typically, the production of butanol is accompanied by the production of acetone.

Thus, advantageously, the fermentation step a) is followed by a butanol isolation step.

This butanol isolation generally consists of separating the various products of the reaction, for example by heteroazeotropic distillation. This separation may also be followed by a distillation intended to obtain the butanol in a more concentrated form.

Another advantage of the process of the invention is that it saves energy: the fermentation step and optional hydrolysis step of the process of the invention are carried out at low temperatures. Their energy cost is also low compared with the cost of extracting butane or benzene.

This energy saving is also accompanied by a reduction in the quantity of $CO_2$ emitted into the atmosphere.

Advantageously, step b) is carried out starting from n-butanol.

A step for separating the n-butanol from other isomers may also be provided. Nevertheless, one advantage of the process is that the fermentation results in a more restricted number of isomers of butanol than the chemical route of propylene hydroformylation. The butanol obtained by fermentation of renewable raw materials is particularly appropriate for carrying out the process of the present invention. In particular, the inventors have shown in Example 1 that the n-butanol derived from a fermentation of renewable raw materials in accordance with step a) has an isobutanol/n-butanol ratio that is lower than for purified butanol derived from fossil raw materials, even before the optional n-butanol isolation step. Since the isobutanol and n-butanol have very similar physicochemical properties, separation of these substances is expensive. Thus, having available n-butanol which is depleted in isobutanol derived from step a) constitutes a major economic advantage for the process forming the subject matter of the invention, since it means that a maleic anhydride of excellent quality can be produced at a lower cost (Examples 2 and 3).

Further, the impurities contained in the mixture obtained at the end of step a), such as butanal, butan-2-ol, n-butylacetate, but-2-en-1-ol and 1,1-dibutoxybutane, at least partially result in the production of maleic anhydride when they undergo oxidation step b). Thus, this constitutes another major economic advantage of the process forming the subject matter of the invention, since it means that a maleic anhydride of excellent quality can be produced while avoiding steps for purifying those impurities.

In step b), butanol is oxidized to produce a gas mixture comprising maleic anhydride.

The oxidation of butanol is carried out in a suitable reactor by passing the gas comprising said butanol over an oxidation catalyst at a temperature that is generally in the range 300° C. to 600° C. Preferably, said reaction is carried out in the presence of air or another gas comprising molecular oxygen, more preferably air, or the other gas comprising the molecular oxygen is present in a large excess.

The catalysts used are generally catalysts based on oxides of vanadium and/or molybdenum. These catalysts may be activated by the addition of oxides of chromium, cerium and/or phosphorus, or even by other conventional activators.

The catalyst may be bulk or deposited or coated onto a suitable support shaped by spraying or deposited directly onto at least one wall of the reactor.

The reaction may be carried out in a fixed bed, a fluidized bed or a circulating fluidized bed.

In a first variation, a catalyst is used that is a mixture of molybdenum trioxide, essentially amorphous titanium dioxide and optionally tungsten trioxide, said oxides being present in proportions of 1 to 8 moles of titanium dioxide for 3 moles of molybdenum trioxide and 0 to 1 mole of tungsten trioxide. Preferably, the specific surface area of the titanium dioxide is more than 150 $m^2/g$, preferably in the range 150 to 250 $m^2/g$. This first variation is generally carried out at a temperature in the range 450° C. to 600° C.; a further advantage is that the reaction is carried out in the adiabatic vapor phase.

In a second variation, a VPO catalyst is used, which is a mixture of at least vanadium oxide and phosphorus, and possibly silica, and the reaction is carried out at a temperature in the range 300° C. to 600° C., preferably in the range 350° C. to 500° C.

The process according to the second variation may also be carried out at a temperature in the range 280° C. to 300° C.; in this case, phthalic anhydride will also advantageously be synthesized.

In a third variation, a bismuth molybdate type catalyst is used; it is a mixture comprising oxides of molybdenum and bismuth and the reaction is carried out at a temperature in the range 300° C. to 600° C., preferably in the range 350° C. to 500° C.

In accordance with a fourth variation, a catalyst is used containing at least molybdenum or vanadium; it is a mixture comprising oxides of molybdenum and vanadium, and the reaction is carried out at a temperature in the range 250° C. to 600° C., preferably in the range 350° C. to 500° C.

Step c) of the process concerns isolation of the maleic anhydride obtained at the end of step b). In particular, when step b) is carried out in accordance with the second variation hereinabove at a temperature in the range 280° C. to 300° C., step c) will comprise a step for separation of maleic anhydride and phthalic anhydride.

The present invention concerns compositions comprising maleic anhydride obtained from matter of renewable origin and uses of the maleic anhydride obtained from matter of renewable origin.

In particular, the present invention concerns the use of maleic anhydride obtained from matter of renewable origin for the manufacture of polymers and for the manufacture of a structure comprising at least one layer of said polymers.

In particular, the present invention concerns the manufacture of the following polymers:
- random copolymers of maleic anhydride with olefins, preferably with ethylene and/or propylene;
- random terpolymers of maleic anhydride, olefins, preferably ethylene and/or propylene, and a co-monomer selected from alkyl acrylate, alkyl methacrylate or vinyl ester;
- copolymers of styrene and maleic anhydride (in solution, in the form of resins or flakes);
- polyolefins, preferably polyethylene and/or polypropylene, grafted with maleic anhydride monomers;
- fluorinated polymers grafted with maleic anhydride monomers;
- polyesters grafted with maleic anhydride monomers;

said polymers comprising maleic anhydride obtained at least in part from matter of renewable origin.

In particular, fluorinated polymers grafted with maleic anhydride monomers are obtained using the process described in application EP 1 484 346; that patent application does not mention the use of maleic anhydride obtained from matter of renewable origin. The fluorinated polymers grafted with maleic anhydride monomers are obtained using the following process:
a) mixing a fluorinated polymer in the molten state with maleic anhydride;
b) forming the mixture obtained in a) into films, plates, granules or powder;
c) subjecting the products obtained in step b), in the absence of air, to photonic ($\gamma$) or electronic ($\beta$) irradiation in a dose in the range 1 to 15 Mrad;
d) optionally, treating the product obtained in c) to eliminate all or a portion of the maleic anhydride that has not been grafted to the fluorinated polymer.

In particular, polyesters grafted with maleic anhydride monomers are obtained using the process described in application WO 97/47670; that patent application does not mention the use of maleic anhydride obtained from matter of renewable origin. The polyesters grafted with maleic anhydride monomers are obtained by a maleic anhydride—polyester addition or substitution reaction.

The maleic anhydride obtained from matter of renewable origin is also advantageously used to prepare 1,4-butanediol and/or $\gamma$-butyrolactone and/or tetrahydrofuran.

A process for preparing these compounds comprises the esterification of maleic anhydride obtained from matter of renewable origin with an alcohol comprising 1 to 5 carbon atoms, advantageously methanol or ethanol, in order to obtain the diester. As an example, dimethyl maleate is obtained with methanol.

Generally, distillation is carried out to isolate the diester.

Hydrogenating dimethyl maleate with an excess of hydrogen at 140° C. and 14 bar over a palladium/alumina catalyst results in the formation of dimethylsuccinate.

Selectively hydrogenating dimethylsuccinate over a copper/zinc oxide catalyst at approximately 225° C. results in the formation of $\gamma$-butyrolactone.

$\gamma$-Butyrolactone is converted to tetrahydrofuran by catalytic dehydration over a silica-alumina catalyst with a high specific surface area in the presence of hydrogen at approximately 200° C.

Hydrogenating $\gamma$-butyrolactone in the presence of an excess of hydrogen over a copper/zinc oxide type catalyst at a high temperature of more than 200° C. results in the formation of 1,4-butanediol.

Example 1

Analysis of Butanol Derived from Fermentation and of Butanol Derived from Fossil Raw Materials The analysis of butanol derived from the fermentation of renewable raw materials and butanol derived from fossil raw materials is illustrated in Table 1 below.

TABLE 1

| | Butanol derived from fermentation of renewable raw materials (analysis before purification) (%) | Butanol derived from fossil raw materials (analysis after purification) (%) |
|---|---|---|
| Butanal | 0.0037 | |
| Butanol-2 | 0.0113 | <0.0010 |
| n-Butyl acetate | 0.0009 | |
| Isobutanol | 0.0662 | 0.0960 |
| n-Butanol | 99.5 | 99.8 |
| 2-Butene-1-ol | 0.1112 | |
| 1,1-Dibutoxybutane | 0.0139 | |

Example 2

Preparation of catalyst A. Catalyst A of type VPO was prepared as described in patent application U.S. Pat. No. 4,769,477 (DuPont). Vanadium oxide was reacted with 100% orthophosphoric acid in a P/V ratio of 1.16, in a mixture of benzyl alcohol and isobutanol under reflux for 16 hours. The blue solid obtained was isolated by filtration, washed with isobutanol and acetone, and dried in air at 110° C. overnight.

1 gram of precursor with a granulometry of 200 to 360 microns was placed in a micro-reactor and activated in situ at 435° C. in a stream of 1.2% of n-butane in air. The flow rate of the gas was 40 mL/minute and the effluents were collected periodically in order to check that the catalyst was stable. After 2 weeks, the catalyst reached a state of equilibrium. The temperature was then reduced to 360° C., and the butanol was injected into the stream of air via a high precision pump.

Example 2a

Comparative

Use of petrochemical butanol containing 0.0960% of isobutanol. The effluent was collected and analyzed. The yield of maleic anhydride was 45% and the quantity of methacrolein methacrylic acid with respect to the maleic anhydride was 180 ppm.

Example 2b

Invention

Use of butanol from fermentation containing 0.0660% of isobutanol. The effluent was collected and analyzed. The yield of maleic anhydride was 45% and the quantity of methacrolein methacrylic acid with respect to the maleic anhydride was 100 ppm.

Example 3

Preparation of catalyst B. Catalyst B was prepared as in the preceding example, but with a P/V ratio of 1.15, and by adding bismuth nitrate at the same time as the vanadium oxide, in a Bi/V ratio of 0.1. In this case, in addition to the $VOHPO_4$-$0.5H_2O$ phase, the precursor contained a $BiPO_4$ phase. The catalyst was activated in a stream of 1.7% of butane in air. After activation, the catalyst contained the phases $(VO)_2P_2O_7$ and $BiPO_4$. The butanol was supplied in the stream of air so as to produce a partial pressure of butanol of 1%. At approximately 360° C., the yield of maleic anhydride was in the range 50% to 60%. As the temperature was progressively increased, yields of phthalic anhydride in the range 10% to 20% were observed intermediate between 250° C. and 350° C.

Example 3a

Comparative

In this example, a partially purified petrochemical n-butanol was used, containing approximately 1.5% of isobutanol. The yield of maleic anhydride was 55%, and the ratio between the quantity of methacrolein+methacrylic acid and maleic anhydride was 2630 ppm.

Example 3b

Invention

In this example, butanol derived from fermentation as in Example 2b was used. The yield of maleic anhydride was 57% and the ratio between the quantity of methacrolein+methacrylic acid and maleic anhydride was 90 ppm.

The invention claimed is:

1. A process for manufacturing maleic anhydride, comprising the following steps:
    a) fermenting renewable raw materials to produce a mixture comprising butanol and optionally purifying said butanol;
    b) oxidizing said butanol to maleic anhydride at a temperature in the range of about 300° C. to 600° C. using a catalyst based on oxides of vanadium and/or of molybdenum; and
    c) isolating the maleic anhydride obtained at the end of step b).

2. The process for manufacturing maleic anhydride as claimed in claim 1, wherein the renewable raw materials are vegetable matter selected from the group consisting of sugar cane, sugar beet, maple, date palm, sugar palm, sorghum, American aloe, corn, durum wheat, barley, rye, wheat, rice, potato, cassava, sweet potato, straw, wood, paper and algae.

3. The process for manufacturing maleic anhydride as claimed in claim 1, wherein the fermentation step a) is followed by a step isolating said butanol.

4. Maleic anhydride obtained from matter of renewable origin, wherein it comprises a quantity of carbon derived from renewable raw materials of more than 20% by weight with respect to the total mass of carbon of the maleic anhydride.

5. Maleic anhydride comprising carbon derived from renewable raw materials of more than 20% by weight with respect to the total mass of carbon of the maleic anhydride prepared by a process comprising:
    a) fermenting renewable raw materials to produce a mixture comprising butanol and optionally purifying said butanol;
    b) oxidizing said butanol to maleic anhydride at a temperature in the range of about 300° C. to 600° C. using a catalyst based on oxides of vanadium and/or of molybdenum; and
    c) isolating the maleic anhydride obtained at the end of step b).

* * * * *